United States Patent
Rudolf

(10) Patent No.: US 10,330,915 B2
(45) Date of Patent: Jun. 25, 2019

(54) BOREHOLE INSPECTION DEVICE

(71) Applicant: JENOPTIK Industrial Metrology Germany GmbH, Villingen-Schwenningen (DE)

(72) Inventor: Michael Rudolf, Constance (DE)

(73) Assignee: JENOPTIK Industrial Metrology Germany GmbH, Villingen-Schwenningen (DE)

(*) Notice: Subject to any disclaimer, the term of this patent is extended or adjusted under 35 U.S.C. 154(b) by 284 days.

(21) Appl. No.: 15/233,420

(22) Filed: Aug. 10, 2016

(65) Prior Publication Data

US 2017/0044889 A1    Feb. 16, 2017

(30) Foreign Application Priority Data

Aug. 12, 2015   (DE) .................... 10 2015 010 225

(51) Int. Cl.
G02B 23/24    (2006.01)
H04N 5/225    (2006.01)
H04N 5/232    (2006.01)

(52) U.S. Cl.
CPC ..... *G02B 23/2415* (2013.01); *G02B 23/2446* (2013.01); *G02B 23/2461* (2013.01);
(Continued)

(58) Field of Classification Search
CPC ................................................. G02B 23/2415
See application file for complete search history.

(56) References Cited

U.S. PATENT DOCUMENTS 4,694,177 A    9/1987 Akai .................. G01T 1/202
                                                    250/366
6,538,371 B1   3/2003 Duggal ............ C09K 11/7774
                                                    252/301.4 H
(Continued)

FOREIGN PATENT DOCUMENTS

CN    103091338 A    8/2013
DE    197 50 698 A1  5/1998
(Continued)

OTHER PUBLICATIONS

"Stereoanalyse und Bildsynthese [Stereo Analysis and Image Synthesis], Springer-Verlag 2005, ISBN 3-540-23439-X" (Abstract/German/English)(4 pages).
(Continued)

*Primary Examiner* — Rowina J Cattungal
(74) *Attorney, Agent, or Firm* — Shlesinger, Arkwright & Garvey LLP

(57) ABSTRACT

Borehole inspection device for inspecting a borehole in a workpiece has a measuring head which includes an endoscope and is insertable into the borehole to be inspected and movable relative to the borehole in different axial positions. Borehole inspection device has an imaging optics with a panoramic view for imaging the inner surface of the borehole, and the imaging optics is in image transmission connection with a digital image recorder. Device has a memory for storing the images recorded in different axial positions of the measuring head, and an evaluation apparatus for evaluating the images stored in the memory. In order to obtain surface depth information about the inner surface of the borehole, the evaluation apparatus is configured for evaluating images recorded at different viewing angles of the imaging optics with regard to the particular surface location, using a 3D reconstruction method.

16 Claims, 2 Drawing Sheets

(52) U.S. Cl.
CPC ....... *G02B 23/2484* (2013.01); *H04N 5/2256* (2013.01); *H04N 5/23238* (2013.01); *H04N 2005/2255* (2013.01)

(56) References Cited

U.S. PATENT DOCUMENTS

| | | | |
|---|---|---|---|
| 6,621,516 B1 | 9/2003 | Wasson | H04N 7/185 348/36 |
| 7,164,476 B2* | 1/2007 | Shima | G01N 21/954 250/559.07 |
| 8,334,971 B2* | 12/2012 | Keller | G01N 21/954 356/237.2 |
| 9,395,310 B2 | 7/2016 | Rudolf | |
| 2003/0104232 A1 | 6/2003 | Kihara et al. | 428/473.5 |
| 2006/0164733 A1 | 7/2006 | Gal | A61B 1/00177 359/725 |
| 2006/0238774 A1 | 10/2006 | Linder | |
| 2008/0093979 A1 | 4/2008 | Bechtel et al. | |
| 2009/0082629 A1 | 3/2009 | Dotan | A61B 1/00096 600/160 |
| 2009/0096413 A1 | 4/2009 | Partovi | H01F 5/003 320/108 |
| 2011/0001984 A1 | 1/2011 | Keller et al. | |
| 2013/0112881 A1 | 5/2013 | Rudolf | |
| 2014/0278111 A1* | 9/2014 | Gerrie | E21B 47/0002 702/8 |
| 2016/0187264 A1 | 6/2016 | Rudolf | |

FOREIGN PATENT DOCUMENTS

| | | |
|---|---|---|
| DE | 198 06 261 B4 | 10/1998 |
| DE | 10 2007 031357 A1 | 3/2009 |
| DE | 10 2008 009975 A1 | 8/2009 |
| DE | 10 2008 002 730 A1 | 12/2009 |
| DE | 10 2009 019459 A1 | 12/2010 |
| DE | 102009019459 A1 | 12/2010 |
| DE | 10 2011 079 067 A1 | 1/2013 |
| DE | 102008009975 B4 | 10/2015 |
| EP | 2 589 953 A2 | 5/2013 |
| JP | S62-108219 A | 5/1987 |
| JP | 2009-125099 A | 6/2009 |
| JP | 2010-172651 A | 8/2010 |
| JP | 2010-261950 A | 11/2010 |
| JP | 2012-112694 A | 6/2012 |
| JP | 2013-096996 A | 5/2013 |
| WO | WO 2009003692 A1 * | 1/2009 .......... G01N 21/954 |
| WO | 2009/003692 A | 8/2009 |
| WO | 2009/150653 A1 | 12/2009 |

OTHER PUBLICATIONS

German Office Action dated Jul. 27, 2016 in German Application No. 10 2015 010 225.7 (6 pages).
Japanese Office Action dated Sep. 6, 2017 in Japanese Counterpart Appliction 2016-157419 (6 pages).
Opposition in German Patent Office against DE 10 2015 010 225 B4, Patentee Jenoptik Industrial Metrology Germany GmbH,"Bore Inspection Device" filed Jun. 21, 2018 (60 pages).
First Office Action in the State Intellectual Property Office of the Peoples Republic of China, Aug. 1, 2018 in Application No. 201610653975.3 Jenoptik Industrial 17 pgs).
Abdalbari et al.,"Endoscopy-MR Image Fusion for Image Guided Procedures," accepted Sep. 13, 2013 Copyright 2013 (10 pages).
Katanacho, Manuel "Detection of Point Correspondence for 3D Reconstruction in Panorama Endoscopy" Masters Thesis, submitted Nov. 21, 2012 (93 pages).
4. Fachseminar: Optische Pruf-und Messverfahren [ . . . ] on Mar. 17-18, 2015, Copyright 2018 DGfZP e.V. (3 pages).
Spinnler et al.,"Automatisierung der technischen Endoskopie mit Hilfe von Methoden der digitalen Bildverarbeitung" http//creativecommons.org./licenses/by-nd/3,0/de/ (18 pages).
Nancy O'Brien et al.,"Axial Motion Stereo" The University of Michigan Computing Research Laboratory1,Jan. 1984 (15 pages).
Gong et al., "Axial-stereo 3D optical metrology of internally machined parts using high-quality imaging from a scannong laser endoscope," Copyright 2014 (4 pages).
Anonymous,"Triangulation," Wikipedia, located at https://en.wikipedia.org/wiki/Triangulation, (last edited) dated Oct. 11, 2018 (2 pages).

\* cited by examiner

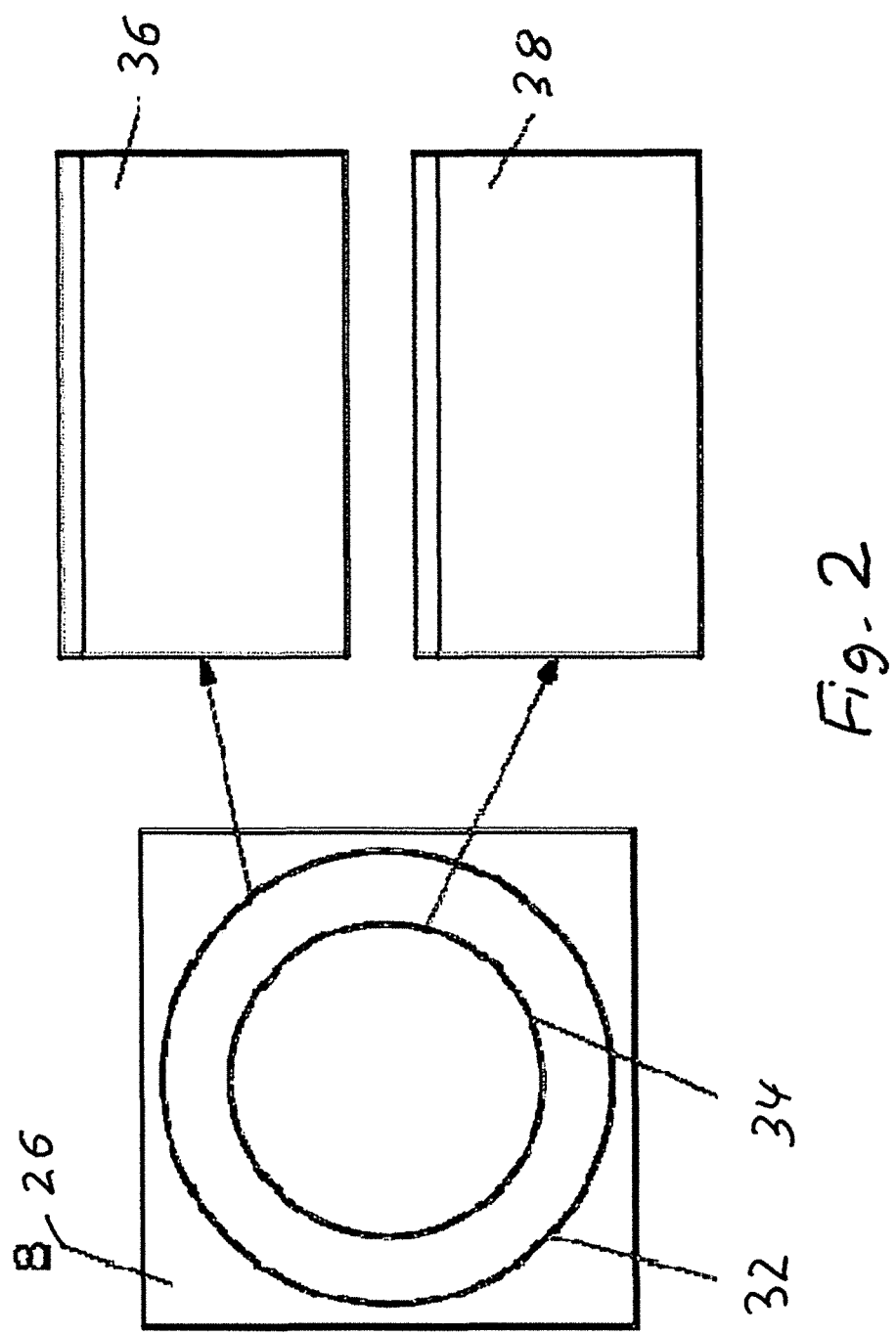

BOREHOLE INSPECTION DEVICE

CROSS-REFERENCE TO RELATED APPLICATIONS

This application claims the priority of German Application No. 10 2015 010 225.7, filed Aug. 12, 2015, which is incorporated herein by reference.

FIELD OF THE INVENTION

The invention relates to a borehole inspection device for inspecting a borehole in a workpiece.

BACKGROUND OF THE INVENTION

Borehole inspection devices of this type, which are also called internal test sensors and also referred to below as devices for short, are used, for example, for borehole inspection in crankcases for internal combustion engines. They are used to image the radial inner surface of the borehole, and, based on the imaging using image processing and pattern recognition methods, to check whether the radial inner surface meets the predetermined requirements for surface quality.

Such devices are known from NO 2009/003692, DE 4416493 A1, DE 4320845 C1, and DE 3232904 C2, for example.

An imaging system for three-dimensional imaging of the interior of an object is known from US 2010/0048995 A1, and may be used, for example, in endoscope-based medical examinations. A medical endoscope is known from US 2014/0055982 A1.

An optical measuring device which operates according to the principle of white light interferometry for measuring surfaces of a measurement object is known from DE 10 2004 045 808 A1.

An interferometric measuring device for measuring the shape of a surface is known from DE 10131780 A1.

A borehole inspection device of the type in question for inspecting a borehole in a workpiece is known from DE 10 2009 019 459 B4, having a measuring head which is designed as an endoscope and is insertable into the borehole to be inspected and movable relative to the borehole in different axial positions, and which has an imaging optics with a panoramic view for imaging the inner surface of the borehole, the imaging optics being in image transmission connection with a digital image recorder. The known device also has a memory for storing the images recorded in different axial positions of the measuring head, and an evaluation apparatus for evaluating the images stored in the memory. The inspection device known from the cited publication allows boreholes to be inspected quickly and accurately.

Similar devices are also known from DE 10 2007 031 358 A1 and DE 10 2008 009 975 A1.

OBJECTS AND SUMMARY OF THE INVENTION

An object of the invention is to provide a device for inspecting a borehole in a workpiece, which is improved with regard to the detection of surface defects on the inner wall of the borehole.

This object is achieved by the invention set forth herein.

The basic concept of the invention lies in modifying the known device in such a way that it is suitable for obtaining surface depth information about the inner surface of the borehole. Obtaining surface depth information is therefore important in the context of the invention, since an anomaly of the surface which is captured in an image of the inner surface, and thus detected, may be either a depression or an elevation. If the anomaly is a depression, a surface defect is possibly present which may make the workpiece which contains the borehole unusable. On the other hand, if the anomaly is an elevation, this may possibly be caused by soiling adhering to an otherwise flawless surface, and which may be removed. Thus, the surface depth information represents important information in the classification and testing of workpieces which are inspected by means of a borehole inspection device.

During the inspection of a borehole, the measuring head of the device according to the invention is inserted into the borehole and moved relative to the borehole in different axial positions. Images are recorded in the different axial positions of the measuring head, and are stored and evaluated in an evaluation apparatus. By using an imaging optics having a panoramic view, i.e., an imaging optics that images the inner surface of the borehole over an angle of 360 degrees in the circumferential direction, according to the invention an image which corresponds to a closed circumferential surface line on the inner surface of the borehole may be imaged on the digital image recorder in any axial position of the measuring head. In the axial direction, this surface line may be linear, for example having a width of only one pixel of the image recorder, or a greater width.

The entire inner surface of the borehole is thus imaged during a complete movement of the measuring head through the borehole, the images recorded in different axial positions of the measuring head being stored in a memory and evaluated by means of an evaluation apparatus. The digital output signals of the image sensor may be converted in particular into a Cartesian image, which is a layout of the inner surface of the borehole. In this regard, reference is made to DE 10 2007 031 358 A1. The resulting Cartesian image may then be examined for detecting anomalies on the inner surface of the borehole, using known image processing and pattern recognition methods.

On this basis, the invention makes use of the fact that a given surface location is recorded at different viewing angles, corresponding to a viewing angle range that is valid for the particular imaging optics during the axial movement of the measuring head. In other words, each surface location on the inner wall is imaged in multiple images, in particular corresponding to the particular axial position of the measuring head at different viewing angles.

On this basis, the invention provides that in order to obtain surface depth information about the particular surface location, the evaluation apparatus is designed and configured for evaluating the images recorded at different viewing angles of the imaging optics with regard to a surface location, using a 3D reconstruction method.

For example and in particular, the stereo triangulation method may be used as the 3D reconstruction method.

In the basic form of the stereo triangulation method, surface depth information about a measuring point is obtained by imaging the measuring point, using two cameras at different viewing angles. Based on the recorded images, the stereo triangulation method may then be used to carry out a 3D reconstruction of the measuring point, i.e., to obtain surface depth information in the context of the invention.

Instead of two cameras, the device according to the invention uses a single digital image recorder having a single imaging optics, but advantageously makes use of the fact that, for example, during the axial movement of the measuring head, the viewing angle of the imaging optics changes with regard to a certain surface location. The images, which for example are recorded in different axial positions of the measuring head and thus at different viewing angles with regard to a surface location, and which are stored in the memory anyway, may then be appropriately used for 3D reconstruction of the surface location, i.e., for obtaining surface depth information at the surface location.

The device according to the invention thus allows not only imaging of the inner surface of the borehole for detecting anomalies, but also, by evaluating the surface depth information obtained from the 3D reconstruction, classifying a detected anomaly as to whether it is a depression or an elevation. Thus, compared to the known device, the information content of the inspection result is increased in a manner that is particularly relevant in practice.

One particular advantage of the device according to the invention is that the surface depth information is obtained anyway from the images recorded during the axial movement of the measuring head, so that obtaining the surface depth information does not require additional time. This is extremely advantageous with regard to short cycle times during the inspection of boreholes. Another advantage of the device according to the invention is that the evaluation apparatus, which is present anyway in devices of the type in question, may be expanded relatively easily with regard to 3D reconstruction.

According to the invention, any suitable 3D reconstruction methods which are based on an evaluation images recorded at different viewing angles may be used. In this regard, one particularly advantageous embodiment of the invention provides that the evaluation apparatus is designed and configured for evaluating the images recorded at different viewing angles with regard to a surface location, according to the stereo triangulation method. The stereo triangulation method allows the recorded images to be evaluated quickly and relatively easily. This method per se is generally known to those skilled in the art. In this regard, reference is made, for example, to Oliver Schreer, *Stereoanalyse und Bildsynthese* [Stereoanalysis and Image Synthesis], Springer-Verlag 2005, ISBN 3-540-43439-X.

Another advantageous further embodiment provides that a feed apparatus which is controllable by a control apparatus is associated with the measuring head in order to set different axial positions, and thus preferably different viewing angles of the imaging optics, with regard to a surface location on the inner wall.

One advantageous further embodiment of the embodiment mentioned above provides that the control apparatus transmits position data, which represent the particular axial position of the measuring head, to the evaluation apparatus in order to associate the particular axial position of the measuring head with an image recorded in this position. In this embodiment, associating an axial position of the measuring head, and thus with regard to a surface location, with the resulting viewing angle of the imaging optics for the image recorded in this axial position is possible in a particularly easy manner.

Another advantageous further embodiment of the invention provides an illumination apparatus for illuminating an imaging area, detected by the imaging optics on the inner surface of the borehole, in light and/or dark field illumination. With regard to the design of the illumination apparatus and the resulting options for illuminating in light and/or dark field illumination, reference is made to DE 10 2008 009 975 A1 and DE 2009 019 459 B4.

A borehole inspection method according to the invention for inspecting a borehole in a workpiece includes that the images recorded at different viewing angles of the imaging optics with regard to a surface location on the inner wall are evaluated by means of a 3D reconstruction method for obtaining surface depth information about the particular surface location, whereby the stereo triangulation method may advantageously be used as the 3D reconstruction method. The same advantages as for the device according to the invention are correspondingly achieved. Advantageous, practical further embodiments of the borehole inspection method according to the invention include anyone one or all of:

a) for obtaining surface depth information about the inner surface of the borehole, images recorded at different viewing angles are evaluated by the stereo triangulation method;

b) the different viewing angles with regard to the particular surface location correspond to different axial positions of the measuring head;

c) the measuring head is moved by means of a feed apparatus which is controllable by a control apparatus in order to set different axial positions, and thus different viewing angles of the imaging optics, with regard to a surface location on the inner wall; and d) the control apparatus transmits position data, which represent a particular axial position of the measuring head, to the evaluation apparatus in order to associate the particular axial position of the measuring head with an image recorded in this position.

In the context of the invention, a borehole is understood to mean any rotationally symmetrical or essentially rotationally symmetrical recess in a workpiece, regardless of how the recess has been introduced in the workpiece, for example by boring or by means of some other machining process, or by molding or the like. In the context of the invention, an essentially rotationally symmetrical recess is understood to mean that the basic form of the recess is rotationally symmetrical, but, for example, may contain grooves or the like. Within the meaning of the invention, a rotationally symmetrical recess naturally is also understood to mean recesses whose basic form deviates from rotational symmetry due to anomalies.

When the terms "axial" or "axial direction" are used in the context of the invention, this means the axial direction of the borehole, which coincides with the axial direction of the imaging optics defined by the optical axis of the imaging optics.

The invention is explained in greater detail below with reference to the accompanying drawings, in which one embodiment of a borehole inspection device according to the invention is illustrated in a highly schematic manner. All features described in the description, illustrated in the drawings, and claimed in the patent claims, alone or in any desired combination, constitute the subject matter of the present invention, regardless of their recapitulation in the specification and claims, and regardless of their description or illustration in the drawings. The disclosed content of the present patent application also encompasses combinations of the claims, and all combinations of individual or multiple claims and features of the claims which are omitted and/or replaced by other features.

Relative terms such as left, right, up, and down are for convenience only and are not intended to be limiting.

BRIEF DESCRIPTION OF THE DRAWINGS

FIG. 2 shows in a highly schematic manner a conversion of an image, recorded by means of the digital image recorder, into a Cartesian image.

DETAILED DESCRIPTION OF THE INVENTION

Figure 1:
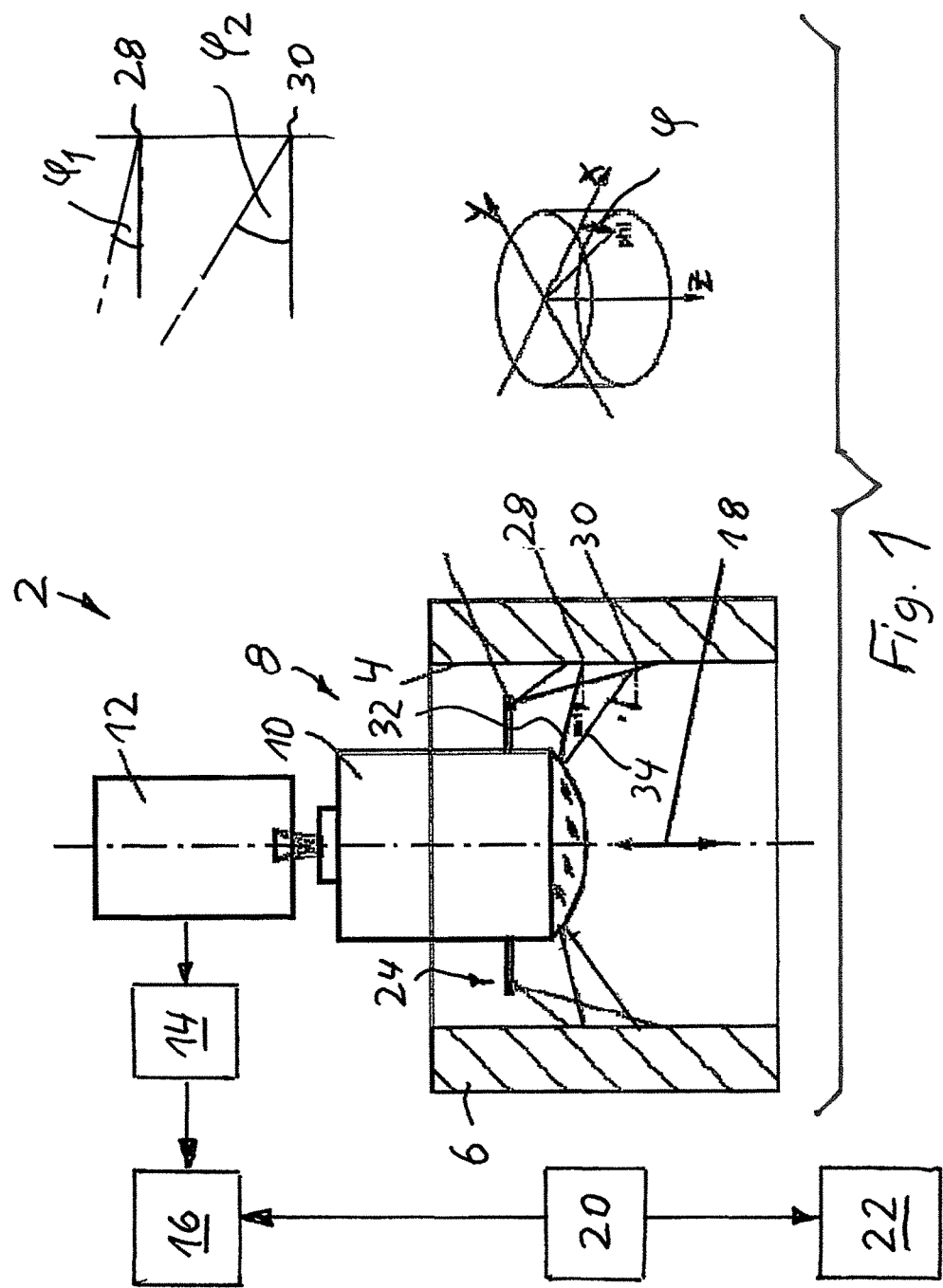
FIG. 1 shows in a highly schematic manner one embodiment of a borehole inspection device according to the invention.

FIG. 1 illustrates one embodiment of a borehole inspection device 2 according to the invention for inspecting a borehole in a workpiece 6, having a measuring head 8 which is designed as an endoscope and is insertable into the borehole 4 to be inspected and movable relative to the borehole 4 in different axial positions, and which has an imaging optics 10 with a panoramic view for imaging the inner surface of the borehole 4. The imaging optics is in image transmission connection with a digital image recorder 12.

The device 2 also has a memory 14 for storing the images recorded in different axial positions of the measuring head 8, the memory 14 being in image transmission connection with the digital image recorder 12.

An evaluation apparatus 16 is provided for evaluating the images stored in the memory 14.

In order to move the measuring head 8 relative to the borehole 4 in the axial direction thereof, and thus to axially position the measuring head 8 (double arrow 18), a feed apparatus 22 which is controllable by a control apparatus 20 is provided for the measuring head 8.

The control apparatus 20 is in data transmission connection with the evaluation apparatus 16, and transmits the particular axial position of the measuring head 8 to the evaluation apparatus 16 in order to associate the particular axial position of the measuring head 8 with an image recorded in this position.

For illumination of an imaging area at the inner surface of the borehole 4 which is detected by the imaging optics 10 in light and/or dark field illumination, an illumination apparatus 24 is provided, which in the embodiment includes a ring-shaped light source, for example with a plurality of LEDs. With regard to the design of the illumination apparatus, reference is made to DE 10 2008 009 975 A1 and DE 10 2009 019 459 A1, the entire contents of which are hereby incorporated into the present patent application.

The mode of functioning of the device 2 according to the invention and of the method according to the invention is as follows:

For inspecting the borehole 4, the measuring head 8 together with the imaging optics 10 (imaging optical system) is inserted into the borehole 4, the measuring head 8 being axially positioned in the direction of the double arrow 18 by means of the feed apparatus 22.

Circumferential surface lines on the inner wall of the borehole 4 are imaged by the imaging optics 10 with a panoramic view, as a circle on the image recorder 12.

FIG. 2 symbolically illustrates the sensor surface, denoted by reference numeral 26. Surface lines at different locations in the z direction of the image recorder 10 are imaged at different viewing angles φ1 and φ2 of FIG. 1. X and y directions, respectively, are likewise shown for reference. General viewing angle φ (phi) is likewise shown for completeness.

FIG. 1 symbolically illustrates two surface lines, denoted by reference numerals 28 and 30. Peripheral beams which adjoin the viewing angle range of the imaging optics 10 are denoted by reference numerals 32, 34 in FIG. 1.

As shown in the top right area in FIG. 1, in the illustrated position of the measuring head 8 the surface line 28 is viewed at the viewing angle φ1, and the surface line 30 is viewed at the viewing angle φ2.

To obtain a complete image of the inner surface of the borehole 4, the measuring head 8 is moved axially relative to the borehole 4, and images are recorded at certain intervals. The camera image is read out circularly in each case, and by polar coordinate transformation is converted line-by-line into a Cartesian image, the images recorded in this way being stored in the memory 14.

FIG. 2 symbolically illustrates how surface lines 32, 34 imaged on the sensor surface 2 of the image recorder 12 are converted into Cartesian images 36, 38.

After the measuring head 8 has been inserted into the borehole 4 in the axial direction until the entire axial depth of the borehole is detected, the images stored in the memory 14 represent the entire inner surface of the borehole 4.

It is apparent that during the axial movement of the measuring head 8, each surface location on the inner wall of the borehole 4 is viewed and imaged at different viewing angles in succession, corresponding to the particular axial position of the measuring head 8. To obtain surface depth information, the images recorded at different viewing angles with regard to the particular surface location are evaluated according to the stereo triangulation method.

If an anomaly is identified on the inner wall of the borehole 4 based on the recorded images, it may be established by means of the surface depth information whether this is a depression and thus a surface defect, or is an elevation possibly caused by soiling of an otherwise flawless surface.

The device 2 according to the invention and the method according to the invention thus allow anomalies to be not only detected, but also classified.

One particular advantage of the device 2 according to the invention and the method according to the invention is that the surface depth information is determined from the images that are recorded anyway during an inspection pass. Therefore, obtaining the surface depth information does not require additional time for the inspection.

Identical or corresponding components are provided with the same reference numerals in the various figures of the drawing. If components are omitted in the figures of the drawing for purposes of representation or illustration, the components in question in the other figures are to be supplemented accordingly. It is apparent to those skilled in the art that the features of the individual embodiments are also exchangeable among the embodiments; thus, the features disclosed with respect to one embodiment may also be identically or correspondingly provided in the other embodiments. It is further apparent to those skilled in the art that the features disclosed in the individual embodiments in each case further embody the invention taken by themselves, i.e., independently of the other features of the particular embodiment.

While this invention has been described as having a preferred design, it is understood that it is capable of further modifications, and uses and/or adaptations of the invention and following in general the principle of the invention and including such departures from the present disclosure as come within the known or customary practice in the art to which the invention pertains, and as may be applied to the central features hereinbefore set forth, and fall within the scope of the invention.

What is claimed is:

1. A borehole inspection device for inspecting a borehole in a workpiece, comprising:

a) a measuring head including an endoscope insertable into a borehole to be inspected and movable relative to the borehole in different positions, and including an imaging optics with a panoramic view for imaging an inner surface of the borehole, and the imaging optics being in image transmission connection with a digital image recorder;
b) a memory for storing the images recorded in different axial positions of the measuring head;
c) an evaluation apparatus for evaluating the images stored in the memory;
d) the evaluation apparatus being configured for evaluating images recorded at different viewing angles of the imaging optics with regard to a particular surface location, using a 3D reconstruction method in order to obtain surface depth information about the inner surface of the borehole; and
e) the evaluation apparatus being configured for evaluating the images recorded at different viewing angles with regard to the particular surface location, using a stereo triangulation method, and the stereo triangulation method being used as the 3D reconstruction method.

2. The borehole inspection device according to claim 1, wherein:
a) the different viewing angles with regard to the particular surface location correspond to different axial positions of the measuring head.

3. The borehole inspection device according to claim 2, wherein:
a) a feed apparatus which is controllable by a control apparatus is associated with the measuring head in order to set different axial positions, and different viewing angles of the imaging optics, with regard to the particular surface location on the inner wall.

4. The borehole inspection device according to claim 3, wherein:
a) the control apparatus transmits position data, which represent the particular axial position of the measuring head, to the evaluation apparatus in order to associate the particular axial position of the measuring head with an image recorded in this position.

5. The borehole inspection device according to claim 1, wherein:
a) an illumination apparatus for illuminating an imaging area, detected by the imaging optics on the inner surface of the borehole, in light and/or dark field illumination.

6. The borehole inspection device according to claim 5, wherein:
a) the different viewing angles with regard to the particular surface location correspond to different axial positions of the measuring head.

7. The borehole inspection device according to claim 1, wherein:
a) a feed apparatus which is controllable by a control apparatus is associated with the measuring head in order to set different axial positions, and thus different viewing angles of the imaging optics, with regard to a surface location on the inner wall.

8. The borehole inspection device according to claim 1, wherein:
a) a feed apparatus which is controllable by a control apparatus is associated with the measuring head in order to set different axial positions with regard to a surface location on the inner wall.

9. A borehole inspection method for inspecting a borehole in a workpiece, comprising:
a) using a measuring head including an endoscope, and having an imaging optics with a panoramic view for imaging the inner surface of the borehole;
b) the imaging optics being in image transmission connection with a digital image recorder, and the measuring head being inserted into the borehole and moved in different axial positions;
c) recording images of the inner surface in different axial positions of the measuring head by the digital image recorder;
d) storing the images recorded in different axial positions of the measuring head in a memory;
e) evaluating the images stored in the memory by an evaluation apparatus;
f) evaluating images recorded at different viewing angles of the imaging optics with regard to a surface location on the inner wall by a 3D reconstruction method for obtaining surface depth information about the particular surface location; and
g) evaluating the images recorded at different viewing angles by the stereo triangulation method for obtaining surface depth information about the inner surface of the borehole, and the stereo triangulation method being used as the 3D reconstruction method.

10. The borehole inspection method according to claim 9, wherein:
a) the different viewing angles with regard to the particular surface location correspond to different axial positions of the measuring head.

11. The borehole inspection method according to claim 9, wherein:
a) the measuring head is moved by means of a feed apparatus which is controllable by a control apparatus in order to set different axial positions, and thus different viewing angles of the imaging optics, with regard to a surface location on the inner wall.

12. The borehole inspection method according to claim 11, wherein:
a) the control apparatus transmits position data, which represents a particular axial position of the measuring head, to the evaluation apparatus in order to associate the particular axial position of the measuring head with an image recorded in this position.

13. The borehole inspection method according to claim 9, wherein:
a) an imaging area detected by the imaging optics on the inner surface of the borehole is illuminated by an illumination apparatus in light and/or dark field illumination.

14. A borehole inspection device for inspecting a borehole in a workpiece, comprising:
a) a measuring head including an endoscope insertable into a borehole to be inspected and movable relative to the borehole in different positions, and including an imaging optics with a panoramic view for imaging an inner surface of the borehole, and the imaging optics being in image transmission connection with a digital image recorder;
b) a memory for storing the images recorded in different axial positions of the measuring head;
c) an evaluation apparatus for evaluating the images stored in the memory;
d) the evaluation apparatus being configured for evaluating images recorded at different viewing angles of the imaging optics with regard to a particular surface location, using a 3D reconstruction method in order to obtain surface depth information about the inner surface of the borehole;

e) the evaluation apparatus being configured for evaluating the images recorded at different viewing angles with regard to the particular surface location, using a stereo triangulation method, and the stereo triangulation method being used as the 3D reconstruction method;

f) the different viewing angles with regard to the particular surface location correspond to different axial positions of the measuring head; and g) a feed apparatus controllable by a control apparatus being associated with the measuring head in order to set different axial positions, and different viewing angles of the imaging optics, with regard to the particular surface location on the inner wall.

15. The borehole inspection device according to claim 14, wherein:

a) the control apparatus transmits position data, which represents the particular axial position of the measuring head, to the evaluation apparatus in order to associate the particular axial position of the measuring head with an image recorded in this position.

16. The borehole inspection device according to claim 14, wherein:

a) an illumination apparatus for illuminating an imaging area, detected by the imaging optics on the inner surface of the borehole, in light and/or dark field illumination.

* * * * *